US00RE39357E

(19) United States
(12) Reissued Patent
Yoneya et al.

(10) Patent Number: US RE39,357 E
(45) Date of Reissued Patent: Oct. 17, 2006

(54) MEDICINE FOR CLOGGING BLOOD VESSELS OF EYE FUNDUS

(75) Inventors: Shin Yoneya, Chou-Ku (JP); Yutaka Yoneda, Tokyo (JP); Masayuki Takasu, Tokyo (JP)

(73) Assignee: Meiji Seika Kaisha, Ltd., Tokyo (JP)

(21) Appl. No.: 10/262,880

(22) Filed: Oct. 3, 2002

Related U.S. Patent Documents

Reissue of:
(64) Patent No.: 6,128,524
Issued: Oct. 3, 2000
Appl. No.: 08/804,191
Filed: Feb. 21, 1997

(30) Foreign Application Priority Data

Feb. 21, 1996 (JP) ..... 8-033195

(51) Int. Cl.
*A61N 5/06* (2006.01)

(52) U.S. Cl. ..... 600/431; 606/4; 606/10; 514/410

(58) Field of Classification Search ..... 606/4, 606/6, 10, 13; 514/410; 600/431; 607/89
See application file for complete search history.

(56) References Cited

U.S. PATENT DOCUMENTS 3,893,447 A * 7/1975 Hockheimer et al.
4,409,979 A * 10/1983 Roussel et al.
4,638,801 A * 1/1987 Dahy et al.
5,633,275 A * 5/1997 Mori et al.
5,705,518 A 1/1998 Richter et al.
5,770,619 A 6/1998 Richter et al.
RE37,180 E 5/2001 Mori et al.

FOREIGN PATENT DOCUMENTS

WO WO 94/12239 6/1994
WO WO 95/24930 9/1995

OTHER PUBLICATIONS

Roberts et al., "Role of Neovasculature and Vascular Permeability on the Tumor Retention of Photodynamic Agents," *Cancer Research 52*:924–930 (1992).
Nelson et al., "In vivo Studies on the Utilization of Mono–L–aspartyl Chlorin (NPe6) for Photodynamic Therapy," *Cancer Research 47*:4681–4685 (1987).
Obana et al., "Quantification of Indocyanine–green Enhancement of Diode Laser Photocoagulation," *J. Japan Ophthalmol. Soc. 97*:581–586 (1993).
STN Data Sheet for the registration of new substance for Registration No. 110230–98–3 (Feb. 24, 1998).
STN Data Sheet for the registration of new substance for Registration No. 220201–39–8 (Mar. 9, 1998).
STN Data Sheet for the registration of new substance for Registration No. 110230–98–3 (Apr. 19, 2000).
STN Data Sheet for the registration of new substance for Registration No. 110230–98–3 (Aug. 26, 2004).
Shuichi Gomi et al., "The Structures of Mono–L–Aspartyl Chlorin e6 and Its Related Compounds," *Heterocycles 48(11)*:2231–2243 (1998).

* cited by examiner

*Primary Examiner*—David M. Shay
(74) *Attorney, Agent, or Firm*—Finnegan, Henderson, Farabow, Garrett and Dunner, L.L.P.

(57) ABSTRACT

An apparatus for clogging blood vessels of an eye fundus includes an illuminating optical system (1) for illuminating an eye fundus of a subject, who has been given an injection of an infrared fluorescent agent, with infrared rays of light and exciting the infrared fluorescent agent so as to generate infrared fluorescence, a photographic optical system (2) for observing and photographing the eye fundus, and a projecting optical system (21) for projecting a laser beam of light having a specific wavelength onto the subject who has been also given an injection of a photosensitive substance which undergoes a photochemical change by the laser beam. In the apparatus, while a region which emits infrared fluorescence is being observed, the laser beam is projected onto the photosensitive substance so as to clog blood vessels of a diseased part in the depth of the eye fundus.

2 Claims, 3 Drawing Sheets

MEDICINE FOR CLOGGING BLOOD VESSELS OF EYE FUNDUS

Matter enclosed in heavy brackets [ ] appears in the original patent but forms no part of this reissue specification; matter printed in italics indicates the additions made by reissue.

BACKGROUND OF THE INVENTION

1. Field of the Invention

This invention relates to a method, apparatus, and medicine for clogging blood vessels of an eye fundus.

2. Description of the Prior Art

There is known a method for clogging blood vessels of an eye fundus. There is also known a photocoagulator used as an apparatus for clogging blood vessels of an eye fundus. In the photocoagulator, an infrared fluorescent agent, called indocyaninegreen, is injected into a subject. When the infrared fluorescent agent circulates through the blood vessels of the eye fundus of the subject, infrared rays of light for excitation are projected onto the eye fundus and, as a result, the infrared fluorescent agent is excited to emit fluorescence. While a region emitting the fluorescence is being observed, a diseased part, such as neovascular vessels of a choroid, in the depth of the eye fundus is specified. After that, a near-infrared semiconductor laser beam is projected onto the diseased part so as to coagulate and treat the diseased part.

In this conventional method and apparatus, however, injury to normal tissues is unavoidable during the treatment because of photocoasulation. Therefore, it is expected to develop a fundus treating method by which a diseased part only is treated to the utmost without injury to normal tissues, and develop an apparatus and a medicine used for the treatment.

SUMMARY OF THE INVENTION

The present invention was made in view of the foregoing. It is therefore an object of the present invention to provide a fundus vessel clogging method by which only a diseased part of an eye fundus is treated to the utmost without injuring normal tissues, an apparatus used for clogging the blood vessels, and a medicine to clog them.

In order to achieve the object, a fundus vessel clogging method according to an aspect of the present invention includes the steps of furnishing a subject with a photosensitive substance which remains in a diseased part in the depth of the eye fundus where an infrared fluorescent agent remains and which undergoes a photosensitive change in the diseased part by the use of a laser beam with a specific wavelength as well as furnishing the subject with the infrared fluorescent agent, specifying the diseased part in accordance with emission of infrared fluorescence, and projecting the laser beam with the specific wavelength onto the diseased part so that the photosensitive substance will produce a photochemical change, thereby clogging blood vessels of the diseased part in the depth of the eye fundus.

In order to achieve the object, a fundus vessel clogging apparatus according to an aspect of the present invention includes an illuminating optical system for illuminating an eye fundus of a subject, who has been furnished with an infrared fluorescent agent, with infrared rays of light so as to excite the infrared fluorescent agent and emit infrared fluorescence, a photographic optical system for observing and photographing the eye fundus, and a projecting optical system for projecting a laser beam with a specific wavelength onto the subject who has been furnished with a photosensitive substance which undergoes a photochemical change by means of the laser beam. In the apparatus, the laser beam is projected onto the photosensitive substance and thereby blood vessels of the diseased part in the depth of the eye fundus are selectively clogged while a region emitting the infrared fluorescence is being observed.

In order to achieve the object, a medicine according to an aspect of the present invention includes a mixture containing an infrared fluorescent agent and a photosensitive substance of the following general formula (CHEMICAL FORMULA 3):

{CHEMICAL FORMULA 3}

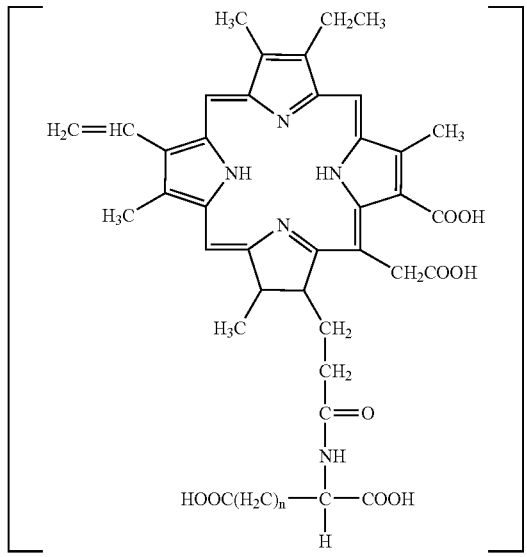

{CHEMICAL 3}

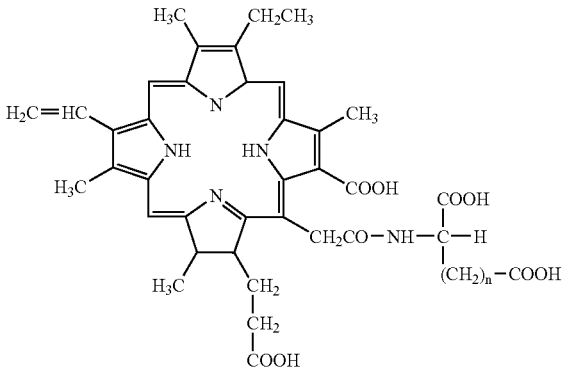

where n is 1 or 2.

In order to achieve the object, a medicine according to another aspect of the present invention includes a mixture containing an infrared fluorescent agent and a photosensitive substance of the following general formula (CHEMICAL FORMULA 4):

{CHEMICAL FORMULA 4}

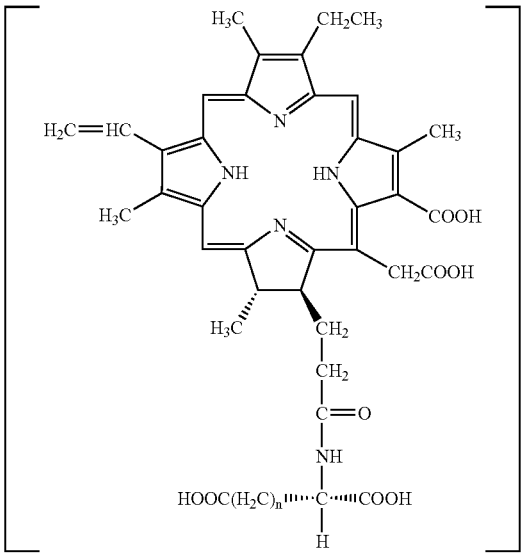

{CHEMICAL FORMULA 4}

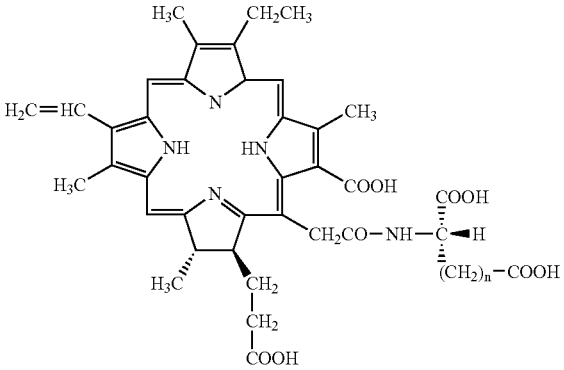

where n is 1 or 2.

A fundus vessel clogging apparatus according to another aspect of the present invention is characterized in that a diseased part in the depth of an eye fundus is specified by infrared fluorescence, and a laser beam with a specific wavelength is projected onto a photosensitive substance which accumulates in the diseased part and undergoes a photochemical change by means of the laser beam for the purpose of treatment for the diseased part.

It is preferable to project an aiming laser beam which serves to distinguish a part where the laser beam is projected from a part where the infrared fluorescence emits in such a way as to superimpose the aiming laser beam upon the laser beam. More preferably, the aiming laser beam is intermittently projected.

According to the present invention, the infrared fluorescent agent and the photosensitive substance remain in the diseased part. In this situation, the remaining of the photosensitive substance in the diseased part is larger than that of the infrared fluorescent agent therein. Therefore, the diseased part is observed and specified by the infrared fluorescent agent, and thereafter a laser beam with a wavelength by which the photosensitive substance produces a photochemical change is projected. Thereby, since only the photosensitive substance produces a photochemical change, an influence on normal tissues is avoided as much as possible, and accordingly the diseased part only can be treated. In this case, if a mixture containing an infrared fluorescent agent and a photosensitive substance is used as a medicine, intravenous injection into the subject can be given at a time.

DETAILED DESCRIPTION OF THE EMBODIMENTS

Figure 1:
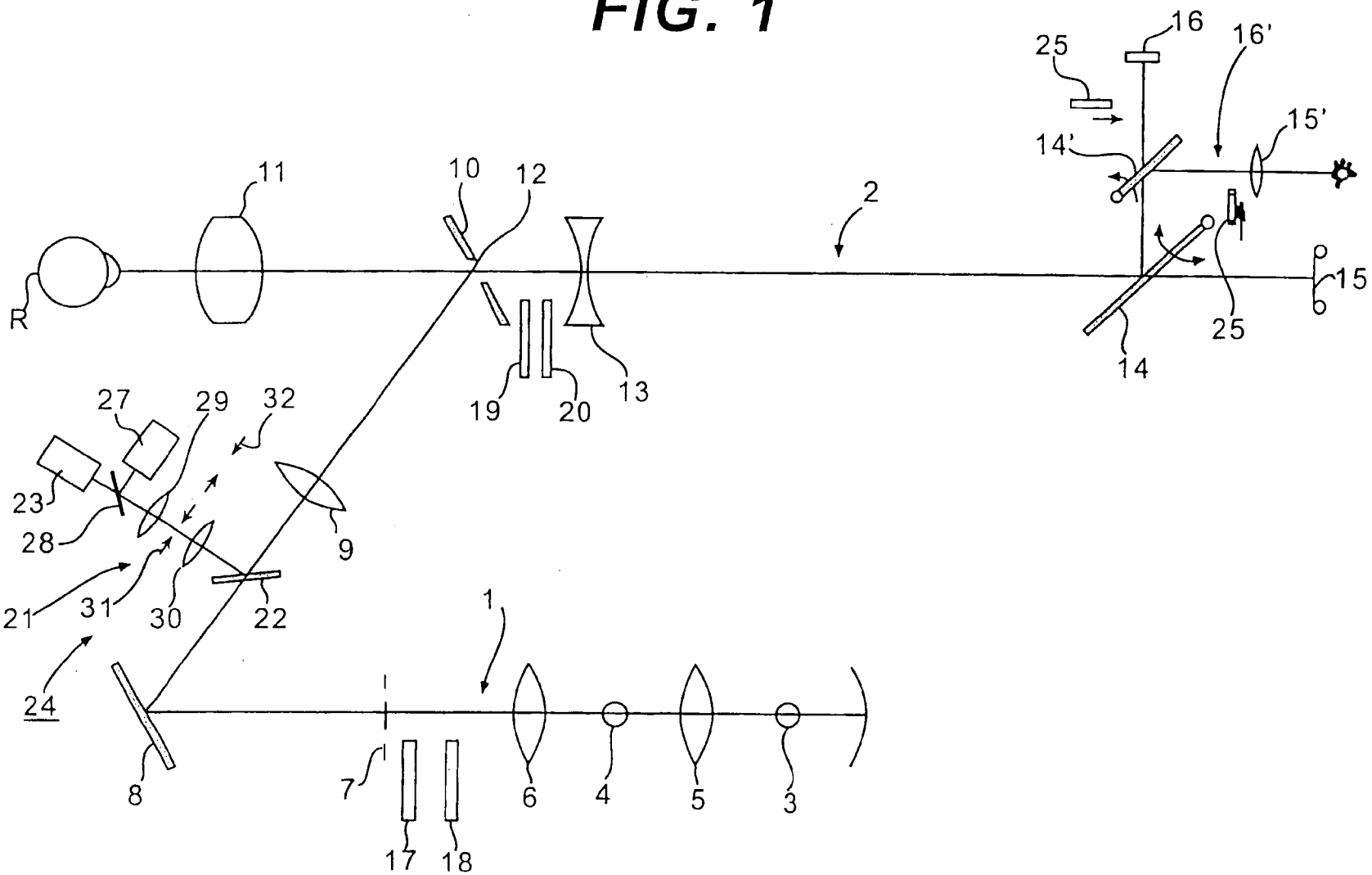
FIG. 1 is a schematic drawing showing optical systems of a fundus blood vessel clogging apparatus according to a first embodiment of the present invention.

FIG. 1 shows an embodiment of a method for clogging blood vessels of an eye fundus and an apparatus, which is applied to a fundus camera, for clogging the blood vessels. In FIG. 1, a reference numeral 1 designates an illuminating optical system of the fundus camera, and reference numeral 2 designates a photographic optical system thereof. The illuminating optical system 1 includes a halogen lamp 3 and a xenon tube 4. The halogen lamp 3 is conjugate to the xenon tube 4 with respect to a condenser lens 5. The illumination light of the halogen lamp 3 and that of the xenon tube 4 are condensed by a condenser lens 6 and then are guided to a reflecting mirror 8 through an annular diaphragm 7. A laser diode may be used instead of the halogen lamp 3.

The illumination light reflected by the reflecting mirror 8 passes through a relay lens 9, is then reflected by a perforated mirror 10, is guided to the eye fundus R of a subject through an objective lens 11, and illuminates the eye fundus R. The light beam from the eye fundus R passes through the objective lens 11 and is then guided to a focusing lens 13 through a hole 12 of the perforated mirror 10. A quick return mirror 14 is disposed behind the focusing lens 13. When a photograph is taken with a film (i.e., when a still image is recorded), the quick return mirror 14 is removed from the optical path of the photographic optical system 2. An image of the fundus is formed on a film 15 by the focusing lens 13. On the other hand, during observation, the light beam from the fundus R is reflected by the quick return mirror 14, and the fundus image is formed on a CCD 16. A signal output of the CCD 16 is converted into an image signal by an image processing circuit (not shown), and the fundus image is formed on a TV monitor (not shown). A surgeon performs an operation, mentioned later, while observing the TV monitor. In the case of visible fluorescence, a fundus image may be observed by the use of a finder optical system 16' which is made up of a quick return mirror 14' and an eyepiece 15'. When the finder optical system 16' is not used, the quick return mirror 14' is placed out of the optical path of light reflected by the quick return mirror 14.

In accordance with a photographic mode, an exciter filter 17 for visible fluorescence and an exciter filter 18 for infrared fluorescence are inserted into the optical path between the annular diaphragm 7 and the condenser lens 6. Correspondingly to the insertion of the exciter filter 17 for visible fluorescence and the exciter filter 18 for infrared fluorescence into the optical path of the illuminating optical system 1, a barrier filter 19 for visible fluorescence and a barrier filter 20 for infrared fluorescence are inserted into the optical path between the perforated mirror 10 and the focusing lens 13 of the photographic optical system 2. When the exciter filter 17 for visible fluorescence is inserted into the optical path of the illuminating optical system 1, green illumination light is guided to the fundus R, and the fundus R is illuminated with the green illumination light. On the other hand, when the exciter filter 11 for infrared fluorescence is inserted into the optical path of the illuminating optical system 1, red and infrared illumination light is guided to the fundus R, and the fundus R is illuminated therewith. In a color photographic mode except the fluorescence photographic mode, the exciter filters 17, 18 are placed out of the optical path of the illuminating optical system 1, and the barrier filters 19, 20 are placed out of the optical path of the photographic optical system 2.

In the optical path of the illuminating optical system 1, there is disposed a reflecting optical member 22 which serves as a constituent part of a laser projection optical system 21 used for photocoagulation between the reflecting mirror B and the relay lens 9. In this embodiment, a half mirror is used as the reflecting optical member 22. The laser projection optical system 21 includes a laser light source 23. Herein, a source for emitting a laser beam having a wavelength range of visible light (wavelength of 664 nm) is used as the laser light source 23. A selective diaphragm 24 is disposed in front of the laser light source 23. The selective diaphragm 24 is conjugate to the fundus R with respect to the objective lens 11. When a blood vessel clogging treatment is conducted, a shutter 25 is inserted between the CCD 16 and the quick return mirror 14 in accordance with the power of a laser beam. The shutter 25 has a function of preventing the CCD 16 from being burned by the reflection of a laser beam having a high power. Likewise, a shutter 25' is inserted into the finder optical system 16'. The laser projection optical system 21 includes a light laser source 27 used for aiming. The laser light source 23 is conjugate to the laser light source 27 with respect to a half mirror 28. Relay lenses 29, 30 are disposed between the half mirror 28 and the reflecting optical member 22.

The selective diaphragm 24 consists of diaphragms 31, 32 which differ in aperture diameter from each other. Either of the selective diaphragms 31, 32 is inserted between the relay lens 29 and the relay lens 30. When a treatment for clogging blood vessels of a diseased part is conducted, a laser spot is formed on the fundus R in accordance with the diameter of an aperture of the selective diaphragm 24. A laser beam emitted by the laser light source 27 is designed to have a wavelength range within which the laser beam can pass through the barrier filter 20. In this embodiment, the wavelength of the laser light source 27 is of a green range.

Since color photography and visible fluorescence photography are not directly relevant to the present invention, an explanation thereof is omitted. Thus, infrared fluorescence photography will be explained.

When the infrared fluorescence photography is carried out, an infrared fluorescent agent, called indocyaninegreen, of the following chemical formula (CHEMICAL FORMULA 5) is injected into the veins of the subject or is taken by the subject in advance.

{CHEMICAL FORMULA 5}

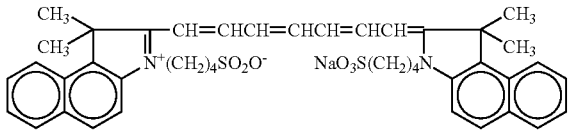

Figure 2:
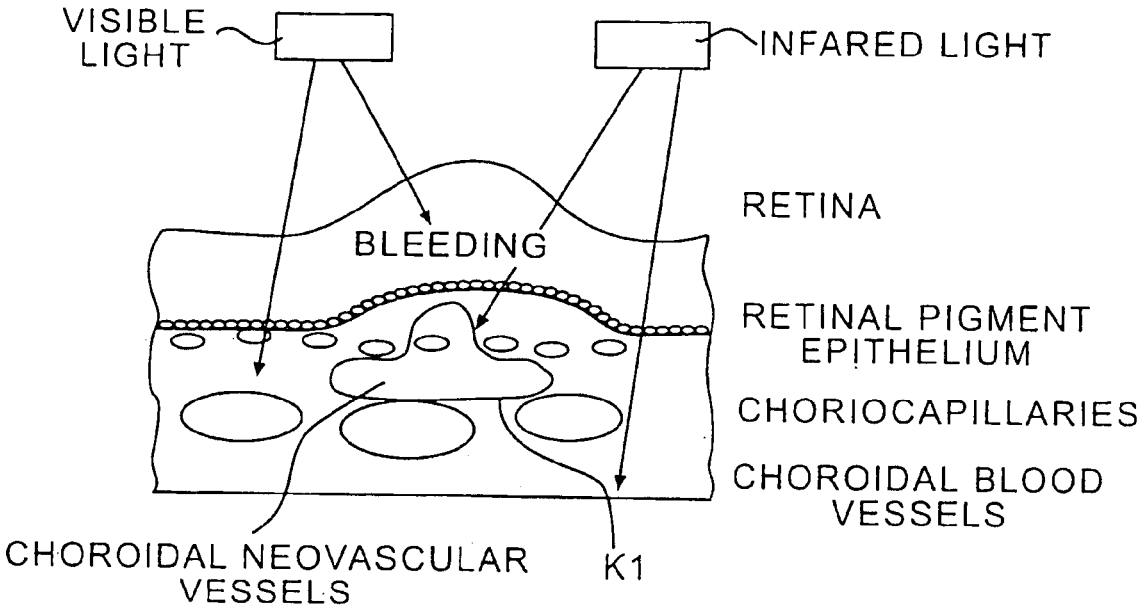
FIG. 2 is a schematic sectional view showing the tissue structure of an eye fundus according to the present invention.

The infrared fluorescent agent circulates through the fundus and is then illuminated with excitation light having a specific wavelength which has passed through the exciter filter 18 for infrared fluorescence. Thereby, infrared fluorescence is emitted. If the fundus R has a diseased part K1, such as neovascular vessels, as shown in FIG. 2, the infrared fluorescent agent remains in the diseased part K1. Thereby, the amount of fluorescence from the diseased part K1 becomes larger than that of fluorescence from around the diseased part K1. Therefore, the diseased part K1 shining brightly on a TV monitor can be located. Conventionally, an infrared laser beam has been projected, taking careful aim, onto the diseased part K1, and thereby the diseased part K1 has been coagulated. However, disadvantageously, this conventional photoagulation method brings about an injury to normal tissues therearound. In the present invention, therefore, a photosensitive substance of the following constitutional formula (CHEMICAL FORMULA 6) is injected into the veins of the subject or is taken by the subject.

{CHEMICAL FORMULA 6}

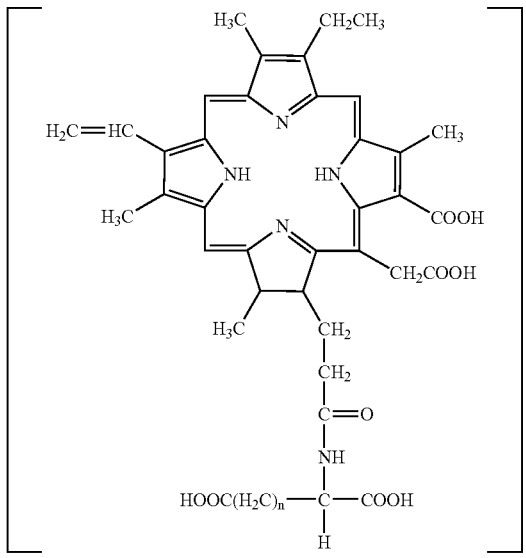

-continued

{CHEMICAL FORMULA 6}

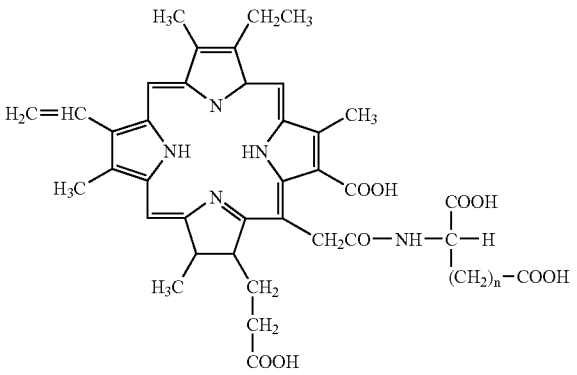

where n is 1 or 2.

This photosensitive substance is a tetrapyrrole derivative, [Mono-L-aspartiru chlorin/e6/4 sodium salt] *Mono-L-aspartyl chlorin e6 tetrasodium salt* (Abbreviated Npe6), one of the tetrapyrrole derivatives, is accumulated together with the infrared fluorescent agent in the endothelium of blood vessels of the diseased part K1 such as neovascular vessels. Active oxygen is then generated by the projection of a laser beam having the wavelength of 664 nm thereonto, and thereby the blood vessels of the diseased part K1 are clogged.

The following formula (CHEMICAL FORMULA 7) is a stereoisomer of CHEMICAL FORMULA 6. It is preferable to use a chemical compound of this formula instead of CHEMICAL FORMULA 6.

{CHEMICAL FORMULA 7}

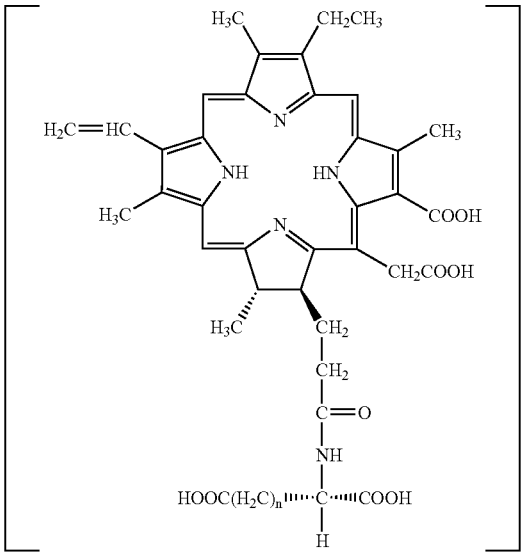

-continued

{CHEMICAL FORMULA 7}

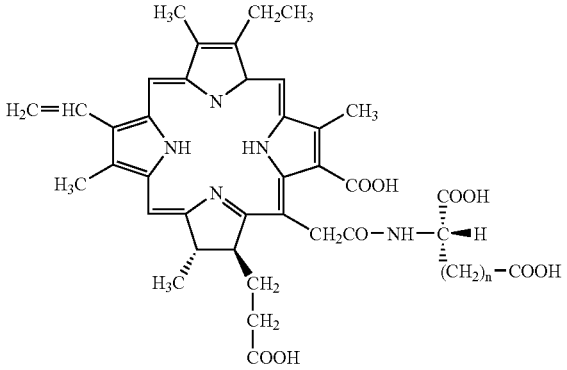

where n is 1 or 2.

The photosensitive substances are mixed with the infrared fluorescent agent, and advantageously a mixture containing them is given to the subject by intravenous injection at a time.

As described above, the laser light source 23 emits a laser beam having the wavelength of 664 nm in order to cause the photosensitive substance to generate a photochemical change. When the diseased part K1 is treated, a laser spot is formed on the fundus R in accordance with the diameter of an aperture of the selective diaphragm 24. The laser power of the laser light source 23 can be regulated by a power regulator (not shown). It is desirable that the laser light source 23 is capable of making the laser oscillation with the projection intensity of 20 to 500 mW/cm$^2$ and with the full power of at least 500 mW.

In the laser projection optical system 21, a laser beam is projected by aiming at a marker which is a region of infrared fluorescence shining brightly in the fundus R. Thereby, the photosensitive substance is caused to generate a photochemical change. Consequently, neovascular vessels can be clogged without injuring normal tissues to the utmost.

Figure 4:
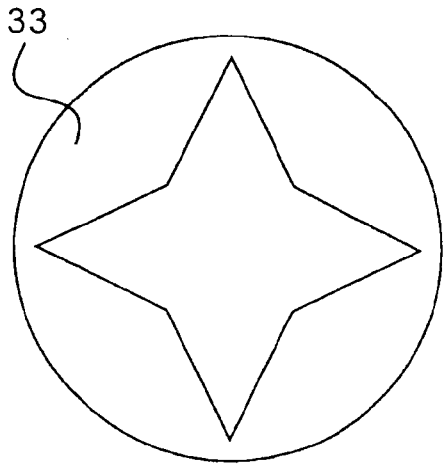
FIG. 4 is a plan view showing a pattern plate of FIG. 3.
Figure 3:
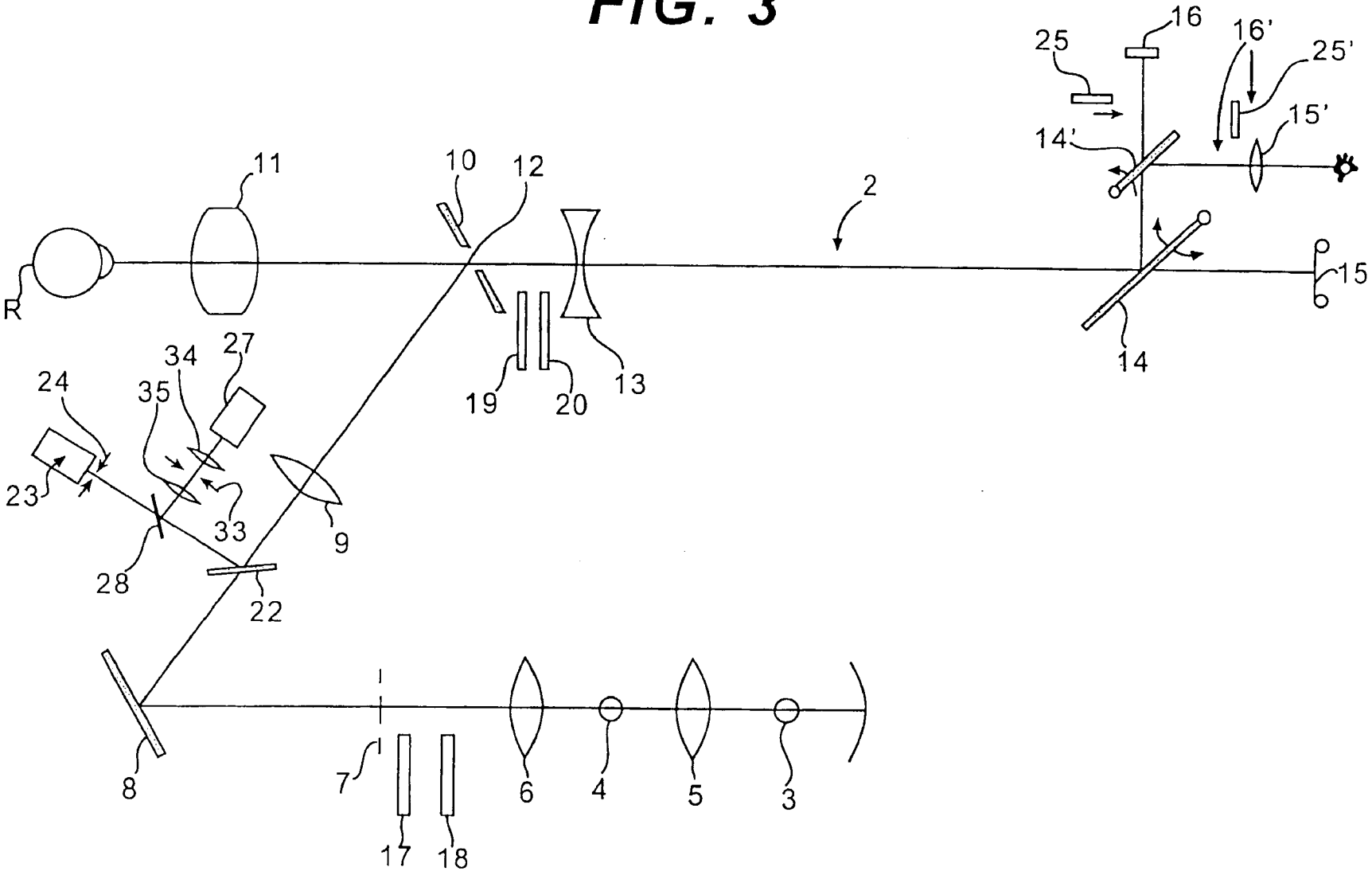
FIG. 3 is a schematic drawing showing optical systems of a fundus blood vessel clogging apparatus according to a second embodiment of the present invention.

FIG. 3 shows a second embodiment of a fundus camera to which the present invention is applied. The fundus camera of the second embodiment is constructed such that a pattern plate 33 is disposed between the laser light source 27 for aiming and the half mirror 28, and the relay to the eye fundus R is made through relay lenses 34, 35. As shown in FIG. 4, for example, a star-shaped aiming pattern is projected onto the pattern plate 33. Thereby, a distinction can be easily drawn between a part where the laser beam is projected and a part where infrared fluorescence is emitted. In order to distinguish the two parts more easily, a construction may be employed in which the laser light source 27 for aiming is intermittently driven to flicker the aiming pattern.

According to the present invention, the method for clogging blood vessels of an eye fundus and the apparatus and medicine used for clogging the blood vessels have the advantage that only the blood vessels of a diseased part are clogged for a surgical treatment almost without injury to normal tissues.

What is claimed is:

1. A medicine including a mixture, the mixture comprising:

an infrared fluorescent agent that remains in a diseased part in a depth of an eye fundus; and a photosensitive substance that remains in the diseased part in the depth of the eye fundus where said infrared fluorescent agent remains for clogging blood vessels at the diseased part by irradiating a laser beam with a specific wavelength to bring about a photochemical change at the diseased part, said photosensitive substance having the following general formula:

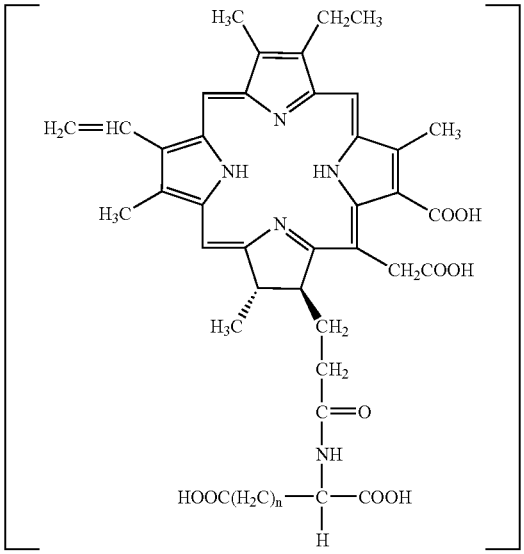

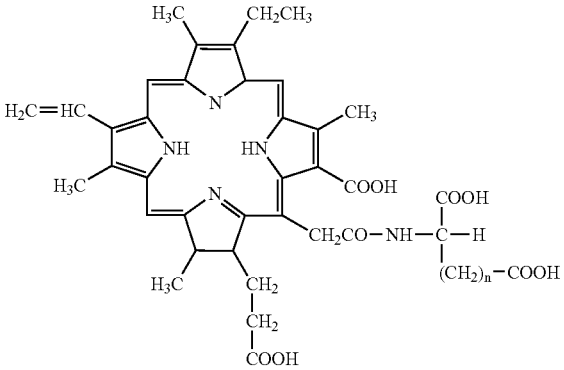

where n is 1 or 2.

2. A medicine including a mixture, the mixture comprising:

an infrared fluorescent agent that remains in a diseased part in a depth of an eye fundus; and a photosensitive substance that remains in the diseased part in the depth of the eye fundus where said infrared fluorescent agent remains for clogging blood vessels at the diseased part by irradiating a laser beam with a specific wavelength to bring about a photochemical change at the diseased part, said photosensitive substance having the following general formula:

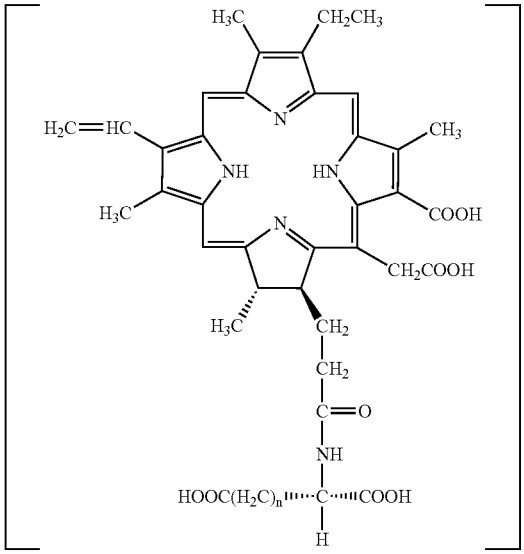

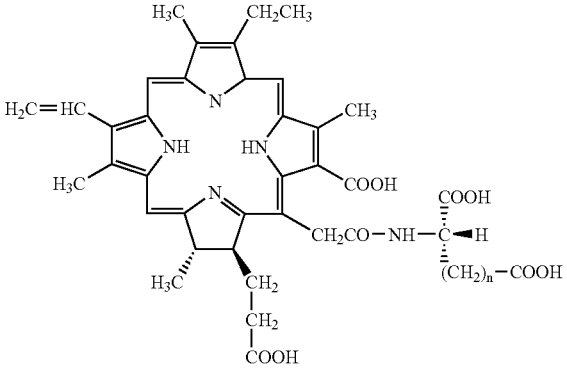

where n is 1 or 2.

* * * * *